United States Patent [19]

Hughes et al.

[11] Patent Number: 5,236,953
[45] Date of Patent: Aug. 17, 1993

[54] ALKENE, ALKYNE OR CYCLOALKYLENE DERIVATIVES

[75] Inventors: Leslie R. Hughes; Howard Tucker, both of Macclesfield, England

[73] Assignee: Imperial Chemical Industries PLC, London, England

[21] Appl. No.: 784,880

[22] Filed: Oct. 30, 1991

Related U.S. Application Data

[62] Division of Ser. No. 337,862, Apr. 14, 1982, Pat. No. 5,084,478, which is a division of Ser. No. 830,136, Feb. 18, 1986, Pat. No. 4,845,119.

[30] Foreign Application Priority Data

Feb. 18, 1985 [GB] United Kingdom ............... 8504093

[51] Int. Cl.$^5$ ............... C07C 255/50; C07C 275/18; C07C 233/21; A61K 31/275
[52] U.S. Cl. ............................ 514/522; 514/597; 514/598; 514/618; 514/630; 558/414; 558/417; 564/47; 564/162; 564/219
[58] Field of Search ............. 558/423, 413, 414, 417; 564/47, 162, 219; 514/522, 598, 618, 630

[56] References Cited

U.S. PATENT DOCUMENTS

| | | | |
|---|---|---|---|
| 4,070,374 | 1/1978 | Chalk et al. | 560/130 X |
| 4,139,561 | 2/1979 | Onopchenko et al. | 260/575 |
| 4,191,775 | 3/1980 | Glen | 424/304 |
| 4,239,776 | 12/1980 | Glen et al. | 424/304 |
| 4,282,218 | 8/1981 | Glen et al. | 424/240 |
| 4,386,080 | 5/1983 | Crossley et al. | 564/173 X |
| 4,507,140 | 3/1985 | Sugavanam | 71/76 |
| 4,532,341 | 7/1985 | Holmwood et al. | 549/559 |
| 4,845,119 | 2/1986 | Hughes et al. | 514/520 X |
| 5,084,478 | 1/1992 | Hughes et al. | 514/520 |

FOREIGN PATENT DOCUMENTS

0193303 9/1986 European Pat. Off. .
52-128329 10/1977 Japan .

OTHER PUBLICATIONS

Parameswara, et al., Synthesis, Communications (1980), pp. 815-818.
Stewart, et al., Biochemistry, 3 (1964), pp. 1998-2004.

*Primary Examiner*—Joseph Paul Brust
*Attorney, Agent, or Firm*—Cushman, Darby & Cushman

[57] ABSTRACT

A compound of the formula

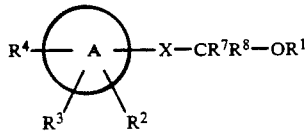

wherein X has the formula $-CR^5=CR^6-$, $-C\equiv C-$ or

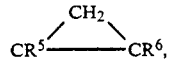

wherein ring A is phenyl, naphthyl or heterocyclic;
wherein $R^1$ is hydrogen, alkyl, alkanoyl or aroyl;
wherein $R^2$, $R^3$ and $R^4$, which may be the same or different, each is an electron withdrawing substituent or each is hydrogen or alkyl, alkoxy or dialkylamino, provided that when ring A is phenyl or naphthyl at least one of $R^2$, $R^3$ and $R^4$ is an electron-withdrawing substituent;
wherein $R^5$ and $R^6$, each is hydrogen, halogeno or alkyl; wherein $R^7$ is alkyl or halogenoalkyl; and wherein $R^8$ has the formula $-Y-Q-R^9$ wherein Y is straight- or branched-chain alkylene or alkenylene; wherein Q is $-O-$, $-S-$, $-SO-$ or $-SO_2-$;
and wherein $R^9$ is alkyl of up to 6 carbon atoms which contains one or more defined substituents, processes for their manufacture and pharmaceutical compositions containing them. The compounds possess antiandrogenic activity and may be used in the treatment of androgen-dependent disease conditions such as prostatic disease, acne, hirsutism or seborrhoea.

7 Claims, No Drawings

ALKENE, ALKYNE OR CYCLOALKYLENE DERIVATIVES

This is a division of application Ser. No. 07/337,682, filed Apr. 14, 1989, now U.S. Pat. No. 5,084,478, which is a Rule 60 division of application Ser. No. 06/830,136, filed Feb. 18, 1986, now U.S. Pat. No. 4,845,119.

This invention relates to novel alkene, alkyne or cycloalkylene derivatives which possess antiandrogenic properties.

Various 4-arylbut-3-en-2-ol derivatives of the general formula:

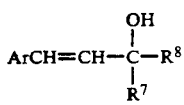

wherein Ar is a phenyl group bearing one or more electron-withdrawing substituents, are known, for a variety of purposes. For example, such compounds wherein $R^7$ is t-butyl and $R^8$ is imidazol-1-ylmethyl or 1,2,4-triazol-1-ylmethyl are known, from European Patent Specifications Nos 40345 and 52424 and other related specifications, as plant growth regulators or fungicides. When $R^7$ and $R^8$ are both methyl the compound wherein Ar is 3-nitrophenyl is known from U.S. Pat. No. 4,139,561, and the compound wherein Ar is 4-chlorophenyl is known from Synthesis, 1980, pages 815–816, in both cases the compounds being used as chemical intermediates. When $R^7$ is methyl, $R^8$ is carboxymethyl or ethoxycarbonylmethyl and Ar is 4-chlorophenyl, the compounds are described in Biochemistry, 1964, Volume 3, pages 1998 et seq., as potential (although inactive) inhibitors of cholesterol biosynthesis.

Various acylanilides of the general formula

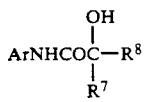

are known as antiandrogens. The compounds wherein $R^7$ and $R^8$ are both methyl and Ar is 4-nitro-3-trifluorophenyl is known as hydroxyflutamide, commercially-available antiandrogen FLUTAMIDE. Other acylanilides which possess antiandrogenic activity are known from European Specifications Nos 2309, 2892 and 40932, and from Japanese Specification No. 52-128329.

According to the present invention there is provided a compound of the formula

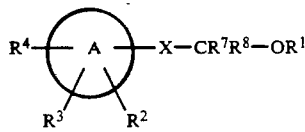

wherein X has the formula

—CR$^5$=CR$^6$—
—C≡C—  or

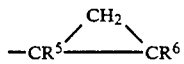

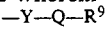

wherein ring A is phenyl, naphthyl or heterocyclic;
wherein $R^1$ is hydrogen, alkyl or alkanoyl each of up to 6 carbon atoms or aroyl of up to 10 carbon atoms;
wherein $R^2$, $R^3$ and $R^4$, which may be the same or different, each is an electron withdrawing substituent selected from halogeno, nitro, cyano and trifluoromethyl, and alkylthio, alkylsulphinyl and alkylsulphonyl each of up to 6 carbon atoms, or each is hydrogen or alkyl, alkoxy or dialkylamino each of up to 6 carbon atoms, provided that when ring A is phenyl or naphthyl at least one of $R^2$, $R^3$ and $R^4$ is an electron-withdrawing substituent;
wherein $R^5$ and $R^6$, which may be the same or different, each is hydrogen, halogeno or alkyl of up to 6 carbon atoms,;
wherein $R^7$ is alkyl or halogenoalkyl each of up to 6 carbon atoms;
and wherein $R^8$ has the formula
—Y—Q—R$^9$ wherein Y is straight- or branched-chain alkylene or alkenylene each of up to 6 carbon atoms;
wherein Q is —O—, —S—, —SO— or —SO$_2$—;
and wherein $R^9$ is alkyl of up to 6 carbon atoms which contains one or more substituents selected from halogeno, cyano, hydroxy, amino, hydroxyimino, guanidino, ureido and carbamoyl;

alkoxy, alkylamino, alkylthio, alkylsulphinyl, alkylsulphonyl, alkylcarbamoyl, alkoxyimino, alkanoyl, halogenoalkanoyl, alkanoylamino and alkylsulphonamido each of up to 6 carbon atoms; alkoxyalkoxy, dialkylamino and dialkylcarbamoyl each of up to 12 carbon atoms;

aryl, aryloxy, arylthio, arylsulphinyl, arylsulphonyl, aryloxyimino and aroyl each of up to 10 carbon atoms; heterocyclyl, heterocyclylthio, heterocyclylsulphinyl, heterocyclylsulphonyl, heterocyclyloxyimino and heterocyclylcarbonyl;

and alkylenedioxy of to 2 to 4 carbon atoms wherein both oxygen atoms are attached to the same carbon atom of $R^9$.

It will be observed that a compound of the invention wherein X is other than ethynylene may exist in two geometrical isomeric forms depending upon the disposition of the various substituents about the olefinic or cycloalkyl bond —X—, and also that a compound of the invention possesses at least one asymmetric carbon atom, namely the carbon atom which bears the substituents $R^7$, $R^8$ and —OR$^1$, and it can therefore exist in racemic and optically-active forms. It is to be understood that this invention encompasses either geometric isomer in racemic form, and any optically-active form of the compound which possesses antiandrogenic activity, it being a matter of common general knowledge how a racemic compound may be resolved into its optically-active forms and how any antiandrogenic activity present in any of these forms may be determined.

A suitable value for ring A when it is heterocyclyl, or for the heterocyclyl, heterocyclylthio-, sulphinyl- or sulphonyl-, heterocyclyloxyimino or heterocyclylcarbonyl substituent in $R^9$ is, for example, a 5- or 6- membered saturated or unsaturated heterocyclic which contains one, two or three hetero atoms selected from oxygen, nitrogen and sulphur, which heterocyclic is a single ring or is fused to one or two benzo-rings or to another heterocyclic ring as defined above, and which heterocyclic is unsubstituted or bears substituents $R^2$, $R^3$ and $R^4$ as defined above, or when a substitutent in $R^9$ may also bear one or more hydroxy, mercapto or amino substituents.

Ring A when heterocyclic is preferably pyridyl, quinolyl or thienyl which is unsubstituted or bears one or two halogeno or cyano substituents, or one nitro substituent.

When $R^9$ is alkyl bearing a heterocyclyl containing substituent the heterocyclyl group is preferably furyl, thienyl, pyridyl, quinolyl, pyrimidinyl, pyrazinyl, thiazolyl, imidazolyl, triazolyl, purinyl, 1,4-benzodioxanyl, pyrazolopyrimidinyl or acridinyl which is unsubstituted or bears one or more substituents selected from halogeno, trifluoromethyl, hydroxy, mercapto and amino, and alkyl and alkoxy each of up to 6 carbon atoms.

A suitable value for $R^1$, $R^2$, $R^3$, $R^4$, $R^5$, $R^6$ or $R^7$ when it is alkyl is, for example, methyl, ethyl, n-propyl, isopropyl, n-butyl or n-hexyl.

A suitable value for $R^1$ when it is alkanoyl, or for the alkanoyl substituent in $R^9$ when $R^9$ is alkyl substituted by alkanoyl is, for example, formyl, acetyl or propionyl.

A suitable value for $R^1$ when it is aroyl, or for the aroyl substituent in $R^9$ when $R^9$ is alkyl substituted by aroyl, is, for example, benzoyl, p-fluorobenzoyl or p-toluoyl.

A suitable value for $R^2$, $R^3$, $R^4$, $R^5$ or $R^6$ when it is halogeno, or for the halogeno substituent in $R^7$ or $R^9$ is, for example, fluoro, chloro or bromo.

A suitable value for $R^2$, $R^3$ or $R^4$ when it is alkoxy, or for the alkoxy substituent in $R^9$ when $R^9$ is alkyl substituted by alkoxy, is, for example, methoxy or ethoxy.

A suitable value for $R^2$, $R^3$ or $R^4$ when it is alkylthio, alkylsulphinyl or alkylsulphonyl, or for the alkylthio, alkylsulphinyl or alkylsulphonyl substituent in $R^9$ when $R^9$ is alkyl substituted by alkylthio, alkylsulphinyl or alkylsulphonyl is, for example, methylthio, ethylthio, n-propylthio, methylsulphinyl, ethylsulphinyl, n-propylsulphinyl, methylsulphonyl, ethylsulphonyl or n-propylsulphonyl.

A suitable value for $R^2$, $R^3$ or $R^4$ when it is dialkylamino, or for the dialkylamino substituent in $R^9$ when $R^9$ is alkyl substituted by dialkylamino is, for example, dimethylamino or diethylamino.

A suitable value for $R^7$ when it is halogenoalkyl is, for example, trifluoromethyl, pentafluoroethyl, heptafluoropropyl, chloromethyl or dichloromethyl.

A suitable value for the alkanoylamino, alkylsulphonamido, alkylamino, alkylcarbamoyl, dialkylcarbamoyl, alkoxyimino, halogenoalkanoyl or alkoxyalkoxy substituent in $R^9$ when $R^9$ is alkyl which bears such a substituent is, for example, acetamido, methylsulphonamido, methylamino, ethylamino, methylcarbamoyl, dimethylcarbamoyl, methoxyimino, chloroacetyl or methoxyethoxy.

A suitable value for the aryl, aryloxy, arylthio, arylsulphinyl, arylsulphonyl or aryloxyimino substituent in $R^9$ when $R^9$ is alkyl which bears such a substituent is, for example, phenyl, naphthyl, tolyl, fluorophenyl, chlorophenyl, methoxyphenyl, nitrophenyl, methylthiophenyl, methylsulphonylphenyl, carbamoylphenyl, acetamidophenyl or dimethylaminophenyl, or the corresponding phenoxy, phenylthio, phenylsulphinyl, phenylsulphonyl, phenoxyimino or substituted phenoxy, phenylthio, phenylsulphinyl, phenylsulphonyl or phenoxyimino.

A preferred compound of the invention has the formula stated above wherein X is $—CR^5\!\!=\!\!CR^6\!\!—$, in the trans- configuration, wherein ring A is phenyl, wherein one or two (the same or different) of $R^2$, $R^3$ and $R^4$ are fluoro, chloro, cyano, trifluoromethyl or nitro, the others of $R^2$, $R^3$ and $R^4$ being hydrogen, wherein $R^1$, $R^5$ and $R^6$ are all hydrogen, wherein $R^7$ is trifluoromethyl, pentafluoroethyl, heptafluoropropyl, chloromethyl or dichloromethyl; wherein Q is —S, —SO— or —SO$_2$, wherein Y is —CH$_2$— and wherein $R^9$ is straight-chain-alkyl of up to 4 carbon atoms which bears one or two substituents selected from chloro, cyano, hydroxy, amino, carbamoyl, methoxy, ethoxy, methylthio, methylsulphonyl, acetyl, acetamido, ureido, dimethylamino, dimethylcarbamoyl, phenyl, fluorophenyl, methylthiophenyl, methylsulphonylphenyl, naphthyl, methoxyphenoxy, phenylthio, methylthiophenylthio, methylsulphonylphenylthio, benzoyl, thenoyl, furyl, pyridyl, pyrazinyl, methylthiazolyl and 1,4-benzodioxanyl; or which bears one such substituent and also three fluorine substituents on the terminal carbon atom; or which bears an ethylenedioxy or trimethylene-1,3-dioxy substituent; or which bears three fluorine substituents on the terminal carbon atom.

A particularly preferred compound of the invention is one defined in the last paragraph above wherein ring A is 3,4-dichlorophenyl, 3-chloro-4-cyanophenyl, 4-cyano-3-trifluoromethylphenyl or 4-fluoro-3-trifluoromethylphenyl and wherein $R^7$ is trifluoromethyl.

Specific compounds of the invention are hereinafter described in the Examples. Of these, preferred compounds by virtue of their high level of antiandrogenic activity are: 1-(3-methoxypropylthio)-, 1-(3-hydroxybutylthio)-, 1-(2-hydroxypropylthio)-, 1-[3,3-(trimethylene-1,3-dioxy)propylthio]-, 1-(2-furylmethylthio)-, 1-(3-oxobutylthio)-, 1-(3,3-ethylenedioxybutylthio)-, 1-(3-hydroxypropylthio)-, 1-(2,3-dihydroxypropylthio-), 1-(2,3-dimethoxypropylthio)-, 1-benzylthio-, 1-(3-phenylpropylthio)-, 1-m-fluorobenzylthio-, 1-p-fluorobenzylthio-, 1-(3-p-methoxyphenylpropylthio)-, 1-(2-carbamoylethylthio)-, 1-(2-N,N-dimethylcarbamoylethylthio)-, 1-(pyrid-3-ylmethylthio)-, 1-(2-methylthiazol-4-ylmethylthio)-, 1-(3-phenoxypropylthio)-, 1-(4-oxo-4-phenylbutylthio)-, 1-[4-oxo-4-(thien-2-yl)butylthio]-, 1-(3-hydroxy-3-phenylpropylthio)-, 1-(3-p-fluorophenyl-3-hydroxypropylthio)-, 1-(3-hydroxy-3-p-methylthiophenylpropylthio)-, 1-(3-hydroxy-3-p-methylsulphonylphenylpropylthio- and 1-(3-hydroxy-3-p-methoxyphenylpropylthio)-4-(4-cyano-3-trifluoromethylphenyl)-2-trifluoromethylbut-trans-3-en-2-ol;

1-(2-carbamoylethylthio)-, 1-(p-methylsulphonylbenzylthio)- and 1-(3-methoxypropylthio)-4-(3-chloro-4-cyanophenyl)-2-trifluoromethylbut-trans-3-en-2-ol; and 1-(3-methylsulphonylpropylsulphonyl)-4-(3,4-dichlorophenyl)-2-trifluoromethylbut-trans-3-en-2-ol.

A compound of the invention may be manufactured by any chemical process known to be suitable for the manufacture of chemically-analogous compounds.

One process for the manufacture of an alkene of the invention wherein $R^1$ is hydroxy and X is $—CR^5\!\!=\!\!CR^6\!\!—$ comprises the reaction of a compound of the formula:

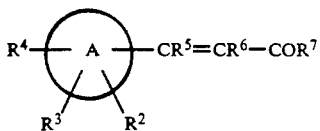

wherein A, $R^2$, $R^3$, $R^4$, $R^5$, $R^6$ and $R^7$ have the meanings stated above, with an organometallic compound of the formula $R^8$-M, wherein $R^8$ has the meaning stated above and M is a metallic group.

M may be, for example, lithium, and the reaction is preferably carried out in an inert diluent or solvent, for example tetrahydrofuran, at a reduced temperature, for example at $-70°$ C. to $-80°$ C.

The starting material for the abovementioned reaction may be obtained by the reaction of an aldehyde or ketone of the formula:

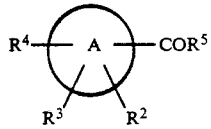

wherein A, $R^2$, $R^3$, $R^4$ and $R^5$ have the meanings stated above, with a compound of the formula
$R^6CH_2COR^7$ or $(Ph)_3P=CR^6COR^7$ or

wherein $R^6$ and $R^7$ have the meanings stated above.

An alternative process for the manufacture of an alkene of the invention wherein $R^1$ is hydroxy, X is $-CR^5=CR^6-$, and Y is $-CH_2-$ comprises the reaction of an epoxide of the formula:

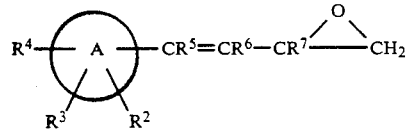

wherein A, $R^2$, $R^3$, $R^4$, $R^5$, $R^6$ and $R^7$ have the meanings stated above, with a compound of the formula $R^9-Q-H$, wherein $R^9$ and Q have the meanings stated above or, when Q is $-S-$, with the corresponding isothiouronium salt of the formula

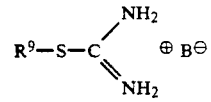

wherein $B^\ominus$ is an anion, for example the chloride, bromide or tosylate ion.

The abovementioned reaction is particularly suitable for the manufacture of an alkene of the invention wherein Q is $-S-$ or wherein the $-H$ atom is otherwise reactive. The reaction is conveniently carried out at laboratory temperature in an inert diluent or solvent, for example tetrahydrofuran or diethyl ether, or, when an isothiouronium salt is used in tetrahydrofuran in the presence of an aqueous base, for example sodium hydroxide solution.

The epoxide starting material may be obtained by the reaction of a compound of the formula:

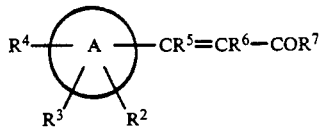

(the preparation of which is described above) with trimethylsulphoxonium iodide in the presence of a base, for example butyl-lithium or, under phase transfer conditions, an alkali metal hydroxide.

A process for the manufacture of a cycloalkylene derivative of the invention wherein X is

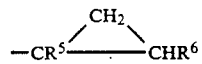

comprises the reaction of a compound of the formula

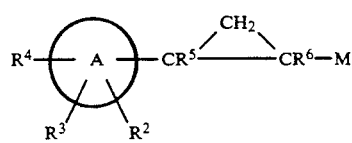

wherein A, $R^2$, $R^3$, $R^4$, $R^5$, $R^6$ and M have the meanings stated above, with a compound of the formula $R^7COR^8$ wherein $R^7$ and $R^8$ have the meanings stated above.

This reaction may be carried out at a low temperature in an inert diluent or solvent. M is preferably lithium.

A process for the manufacture of an alkyne of the invention wherein X is $-C\equiv C-$ comprises the reaction of a compound of the formula

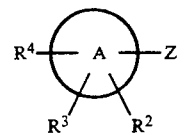

wherein A, $R^1$, $R^2$, $R^3$ and $R^4$ have the meanings stated above and wherein Z is a displaceable group, with a compound of the formula $HC\equiv C-CR^7R^8OR^1$ wherein $R^1$, $R^7$ and $R^8$ have the meanings stated above.

A suitable value for Z is, for example, an iodo group.

A compound of the invention wherein X is $-C\equiv C-$ may be reduced to the corresponding compound of the invention wherein X is $-CH=CH-$. Conventional conditions for the reduction may be chosen so that either the cis- or trans- alkene is obtained.

Various interconversions of compounds of the invention wherein $R^9$ has different meanings are possible. Thus, for example (i) a compound wherein $R^9$ bears an amino substituent may be acylated to give the corresponding compound wherein R$^9$ bears an alkanoylamino, alkoxycarbonylamino or alkylsulphonamido substituent;

(ii) a compound wherein R$^9$ is alkyl substituted by alkanoyl may be reduced to the corresponding compound wherein R$^9$ is hydroxyalkyl.

A compound of the invention wherein R$^1$ is alkyl may be prepared by the alkylation of the corresponding compound wherein R$^1$ is hydrogen.

A compound of the invention wherein R$^1$ is alkanoyl or aroyl may be prepared by the acylation of the corresponding compound wherein R$^1$ is hydrogen.

A compound of the invention wherein one or more of R$^2$, R$^3$, R$^4$ and a substituent in R$^9$ is alkylsulphinyl or alkylsulphonyl, or a substituent in R$^9$ is arylsulphinyl, arylsulphonyl, heterocyclylsulphinyl or heterocyclylsulphonyl, or Q is —SO— or —SO$_2$—, may be prepared by the oxidation of the corresponding compound wherein one or more of R$^2$, R$^3$, R$^4$ and a substituent in R$^9$ is alkylthio, arylthio or heterocyclylthio, or Q is —S—, respectively. The oxidising agent and conditions used will determine whether a sulphinyl or a sulphonyl compound is obtained. Thus, oxidation with sodium metaperiodate in methanol solution at or below laboratory temperature will generally convert a thio compound into the corresponding sulphinyl compound; and oxidation with hydrogen peroxide in acetic acid solution or with a persulphate in aqueous solution at or above laboratory temperature, will generally convert a thio compound into the corresponding sulphonyl compound, although this reaction occasionally stops at the sulphinyl stage.

As stated above, a compound of the invention possesses antiandrogenic properties as demonstrated by its ability to decrease the weight of the seminal vesicles of a castrated male rat when administered concurrently with testosterone propionate. A compound of the invention may therefore be used in the treatment of, for example, malignant or benign prostatic disease or of androgen dependent disease conditions, such as acne, hirsutism or seborrhoea, in warm-blooded vertebrates including man. It may also be used to improve ovulation in a domestic animal.

At a dose of a compound of the invention which produces antiandrogenic activity in rats no symptom of toxicity is apparent.

The compound of the invention may be administered to a warm-blooded animal in the form of a pharmaceutical or veterinary composition which comprises the compound in association with a pharmaceutically-acceptable diluent or carrier.

The composition may be in a form suitable for oral dosage, as a tablet, capsule, aqueous or oily solution or suspension, or emulsion. It may alternatively be in the form of a sterile solution or suspension suitable for parenteral administration, or be in the form of an ointment or lotion for topical administration, or be in the form of a suppository.

The composition may additionally contain one or more drugs selected from anti-oestrogens, for example tamoxifen; aromatase inhibitors, for example testolactone or aminoglutethimide; progestins, for example medroxyprogesterone acetate; inhibitors of gonadotrophin secretion, for example danazol; LH—RH analogues, for example buserelin; cytotoxic agents, for example cyclophosphamide; antibiotics, for example penicillin or oxytetracyclin; and anti-inflammatory agents, for example, especially for topical use, fluocinolone acetonide.

The compound of the invention will normally be administered to a warm-blooded animal at a dose of between 0.1 mg. and 125 mg. per kg. bodyweight.

The invention is illustrated but not limited by the following Examples:

EXAMPLE 1

A solution of 4-(3,4-dichlorophenyl)-1,2-epoxy-2-trifluoromethylbut-trans-3-ene (0.3 g.) in tetrahydrofuran (5 ml.) was added dropwise to a stirred mixture of 2-methylthioethanethiol (0.2 g.) and sodium hydride (0.08 g. of a 50% dispersion in mineral oil) in tetrahydrofuran (25 ml.) and the mixture was stirred at laboratory temperature for 1.5 hours and then poured into water. The mixture was extracted with ethyl acetate and the extract was washed with saturated aqueous sodium chloride solution, dried over magnesium sulphate and evaporated to dryness under reduced pressure. The residue was purified by chromatography on a silica gel column using a 3:2 v/v mixture of petroleum ether (b.p. 60°–80° C.) and methylene chloride as eluant. There was thus obtained as an oil 4-(3,4-dichlorophenyl)-1-[(2-methylthioethyl)thio]-2-trifluoromethylbut-trans-3-en-2-ol, m.p. 64° C.

The epoxybutene used as starting material was obtained as follows: A solution of 3,4-dichlorobenzaldehyde (10 g.) in ethanol (50 ml.), and then 1,1,1-trifluoroacetone (6.5 ml.), were successively added to a stirred suspension of freshly ground lithium hydroxide monohydrate (1.0 g.) in ethanol (100 ml.), the trifluoroacetone being added by injection below the surface of the reaction mixture, and the mixture was stirred for 1 hour and then poured into water (600 ml.). The mixture was extracted with ethyl acetate and the extract was washed with aqueous 2N-hydrochloric acid and then saturated aqueous sodium chloride solution, dried over magnesium sulphate and evaporated to dryness under reduced pressure. The residue was purified by chromatography on a silica gel column using a 7:3 v/v mixture of petroleum ether (b.p. 60°–80° C.) and methylene chloride as eluant. There was thus obtained 1,1,1-trifluoro-4-(3,4-dichlorophenyl)but-trans-3-en-2-one, m.p. 81° C.

n-Butyl-lithium (11.6 ml. of a 1.6 molar solution in hexane) was added dropwise to a stirred suspension of trimethylsulphoxonium iodide (4.1 g.) in tetrahydrofuran (200 ml.) which was cooled to −10 C., and the mixture was stirred at that temperature for 2 hours and then added to a stirred solution of 4-(3,4-dichlorophenyl)-1,1,1-trifluorobut-trans-3-en-2-one (2.0 g.) in tetrahydrofuran (100 ml.). The mixture was stirred for 90 minutes, saturated aqueous ammonium chloride solution (75 ml.) was added and the mixture was partitioned between water and ethyl acetate. The layers were separated, the aqueous layer was extracted with ethyl acetate and the combined ethyl acetate solutions were washed with saturated aqueous sodium chloride solution, dried over magnesium sulphate and evaporated to dryness under reduced pressure. The residue was purified by chromatography on a silica gel column using a 4:1 v/v mixture of petroleum ether (b.p. 60°–80° C.) and methylene chloride as eluant. There was thus obtained as an oil 4-(3,4-dichlorophenyl)-1,2-epoxy-2-trifluoromethyl-but-trans-3 ene.

The process described above was repeated using the appropriate thiol and the appropriate epoxide, prepared from the appropriate butenone either as described above or by the method generally described in Angewandte Chemie (International Edition), 1973, Volume 12, page 845. There were thus obtained the compounds described in the following table:

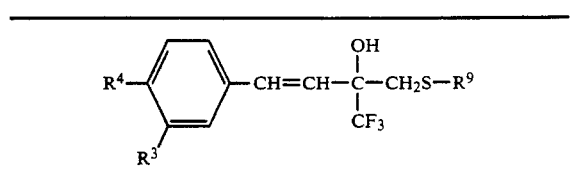

| $R^3$ | $R^4$ | $R^9$ | m.p. (°C.) | Note |
|---|---|---|---|---|
| Cl | Cl | $CH_2CHOHCH_2OH$ | (oil) | |
| $CF_3$ | CN | $CH_2CHOHCH_2OH$ | (oil) | 1 |
| Cl | Cl | $(CH_2)_2CHOHCH_3$ | (oil) | |
| $CF_3$ | CN | $(CH_2)_2CHOHCH_3$ | (oil) | 1 |
| Cl | Cl | $(CH_2)_2OH$ | 112–113 | |
| $CF_3$ | CN | $(CH_2)_2OH$ | (oil) | 1 |
| Cl | Cl | $CH_2CHOHCF_3$ | (oil) | |
| $CF_3$ | CN | $CH_2CHOHCF_3$ | (oil) | 1 |
| Cl | Cl | $CH_2CHOHCH_3$ | (oil) | |
| $CF_3$ | CN | $CH_2CHOHCH_3$ | (oil) | 1 |
| $CF_3$ | CN | $(CH_2)_2CH\overset{O}{\underset{O}{\diamond}}(CH_2)_3$ | (oil) | 1 |
| Cl | Cl | $(CH_2)_2C(CH_3)\overset{O}{\underset{O}{\diamond}}(CH_2)_2$ | (oil) | |
| $CF_3$ | CN | $(CH_2)_2C(CH_3)\overset{O}{\underset{O}{\diamond}}(CH_2)_2$ | (oil) | 1 |
| $CF_3$ | CN | $(CH_2)_2COCH_3$ | (oil) | 1 |
| Cl | Cl | $(CH_2)_2COCH_3$ | (oil) | |
| Cl | Cl | $(CH_2)_2CONH_2$ | 76 | |
| Cl | CN | $(CH_2)_2CONH_2$ | (oil) | |
| $CF_3$ | CN | $(CH_2)_2CONH_2$ | (oil) | 1 |
| Cl | CN | $(CH_2)_2OCH_3$ | 54–55 | 1 |
| Cl | Cl | $(CH_2)_2N(CH_3)_2$ | (oil) | |
| Cl | CN | $(CH_2)_2SCH_3$ | (oil) | 1 |
| Cl | Cl | $(CH_2)_3SCH_3$ | (oil) | |
| Cl | CN | $(CH_2)_3SCH_3$ | (oil) | 1 |
| $CF_3$ | CN | $(CH_2)_3SCH_3$ | (oil) | 1 |
| Cl | CN | $(CH_2)_2NHCOCH_3$ | (oil) | 1 |
| Cl | Cl | $(CH_2)_2NHCONH_2$ | 118–130 | |
| Cl | Cl | $CH_2C_6H_5$ | (oil) | |
| $CF_3$ | CN | $CH_2C_6H_5$ | 80–84 | |
| Cl | Cl | $(CH_2)_2$-4-fluorophenyl | (oil) | |
| Cl | Cl | $CH_2$-1-naphthyl | (oil) | |
| Cl | Cl | $CH_2$-2-furyl | (oil) | |
| $CF_3$ | CN | $CH_2$-2-furyl | (oil) | 1 |
| Cl | Cl | $(CH_2)_2NH_2$ | 137–138 | |
| Cl | Cl | $(CH_2)_2$-2-pyrazinyl | (oil) | |
| $CF_3$ | CN | $(CH_2)_2$-2-pyrazinyl | (oil) | 1 |
| $CF_3$ | CN | $(CH_2)_3O$-4-methoxyphenyl | (oil) | 1 |
| $CF_3$ | CN | $(CH_2)_2CON(CH_3)_2$ | (oil) | 1 |
| $CF_3$ | CN | $(CH_2)_3CON(CH_3)_2$ | (oil) | 1 |
| $CF_3$ | CN | $(CH_2)_2C_6H_5$ | 58–60 | 1 |
| $CF_3$ | CN | $(CH_2)_2$-4-methylthiophenyl | (oil) | 1 |
| $CF_3$ | CN | $CH_2$-2-pyridyl | (oil) | 1 |
| $CF_3$ | CN | $(CH_2)_2$-2-pyridyl | (oil) | 1 |
| $CF_3$ | CN | $CH_2$-(1,4-benzodioxan-2-yl) | (oil) | 1 |
| $CF_3$ | CN | $CH_2CHOHC_6H_5$ | (oil) | 1 |
| $CF_3$ | CN | $CH_2CHOH$-4-methyl-sulphonylphenyl | (oil) | 1 |
| $CF_3$ | CN | $CH_2CHOH$-3-pyridyl | (oil) | |

-continued

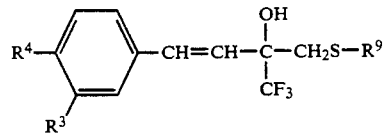

| $R^3$ | $R^4$ | $R^9$ | m.p. (°C.) | Note |
|---|---|---|---|---|
| $CF_3$ | CN | 4-fluorophenyl $(CH_2)C\overset{O}{\underset{O}{\diamond}}(CH_2)_2$ | (oil) | 1 |
| $CF_3$ | CN | $(CH_2)_2CO$-4-fluorophenyl | (oil) | 2 |

Note 1
The butenone starting material was obtained by the reaction of the appropriate aldehyde with diethyl 3,3,3-trifluoro-2-methyliminopropylphosphonate by the method described in Tetrahedron Letters (1983), page 4229. 4-(4-Cyano-3-trifluoromethylphenyl)-1,1,1-trifluorobut-3-en-2-one has m.p. 119–121° C. and 4-(3-chloro-4-cyanophenyl)-1,1,1-trifluorobut-3-en-2-one has m.p. 102–104° C.

Note 2
Prepared by acid hydrolysis of the preceding compound.

EXAMPLE 2

A solution of sodium hydroxide (0.06 g) in water (0.5 ml.) was added dropwise to a stirred suspension of 3-hydroxy-3-phenylpropylisothiouronium chloride (0.18 g.) in tetrahydrofuran which was maintained at laboratory temperature under an atmosphere of argon, and the mixture was stirred for 15 minutes. A solution of 4-(4-cyano-3-trifluoromethylphenyl)-1,2-epoxy-2-trifluoromethylbut-trans-3-ene (0.205 g.) in tetrahydrofuran (2 ml.) was added and the mixture was stirred at laboratory temperature for 20 hours, diluted with ethyl acetate (20 ml.) and washed with saturated aqueous sodium chloride solution (15 ml.). The organic solution was dried over magnesium sulphate and evaporated to dryness and the residue was purified by flash chromatography on a silica gel (Merck 9385) column using a 2:1 v/v mixture of petroleum ether (b.p. 60°–80° C.) and ethyl acetate as eluent. There was thus obtained, as an oil, 4-(4-cyano-3-trifluoromethylphenyl)-1-(3-hydroxy-3-phenylpropyl)thio-2-trifluoromethylbut-trans-3-en-2-ol.

The process described above was repeated using the appropriate isothiouronium chloride (or bromide indicated by an asterisk * in the table, or tosylate, indicated by two asterisks ** in the table) and the appropriate epoxide as starting materials and there were thus obtained the compounds described in the following table:

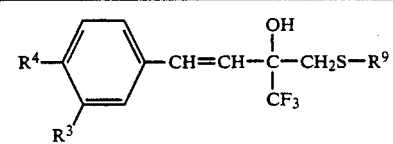

| $R^3$ | $R^4$ | $R^9$ | m.p. (°C.) |
|---|---|---|---|
| Cl | Cl | $(CH_2)_3CF_3$ | (oil) |
| Cl | CN | $(CH_2)_3CF_3$ | (oil) |
| Cl | Cl | $(CH_2)_2OCH_3$ | (oil) |
| Cl | Cl | $(CH_2)_3OCH_3$ | (oil) |
| $CF_3$ | F | $(CH_2)_3OCH_3$ | (oil) |
| Cl | CN | $(CH_2)_3OCH_3$ | (oil) |
| $CF_3$ | CN | $(CH_2)_3OCH_3$ | (oil) |
| Cl | CN | $(CH_2)_4OCH_3$ | (oil) |
| Cl | CN | $(CH_2)_3OC_2H_5$ | (oil) |

-continued

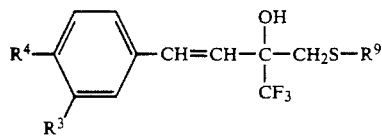

| R³ | R⁴ | R⁹ | m.p. (°C.) |
|---|---|---|---|
| CF₃ | CN | (CH₂)₃OC₂H₅ | (oil) |
| Cl | Cl | (CH₂)₂CN | (oil) |
| Cl | Cl | (CH₂)₃CN | (oil) |
| CF₃ | CN | (CH₂)₃C₆H₅ | (oil)* |
| CF₃ | CN | (CH₂)₂-3-methylthio-phenyl | (oil) |
| CF₃ | CN | CH₂-3-methylsulphonyl-phenyl | (oil) |
| CF₃ | CN | CH₂-4-methylsulphonyl-phenyl | (oil) |
| CF₃ | CN | CH₂-4-fluorophenyl | (oil) |
| CF₃ | CN | CH₂-3-pyridyl | (oil) |
| CF₃ | CN | CH₂-4-pyridyl | 133-134 |
| CF₃ | CN | CH₂-(2-methylthiazol-4-yl) | (oil) |
| CF₃ | CN | CH₂CH(OCH₃)CH₂OCH₃ | (oil)** |
| CF₃ | CN | (CH₂)₂CHOH-4-fluoro-phenyl | 82-86 |
| CF₃ | CN | (CH₂)₂O-4-methyl-sulphonylphenyl | (oil)* |
| CF₃ | CN | (CH₂)₂SC₆H₅ | 59-62 |
| CF₃ | CN | (CH₂)₂S-3-methyl-sulphonylphenyl | (oil) |
| CF₃ | CN | (CH₂)₃SC₆H₅ | (oil) |

EXAMPLE 3

Aqueous 2N-sodium hydroxide solution (0.75 ml.) was added dropwise to a stirred suspension of 3-hydroxy-3-p-methoxyphenylpropylisothiouronium bromide (0.236 g.) and 4-(4-cyano-3-trifluoromethylphenyl)-1,2-epoxy-2-trifluoromethylbut-trans-3-ene (0.205 g.) in tetrahydrofuran which was maintained at laboratory temperature under an atmosphere of argon, and the mixture was stirred at laboratory temperature for 20 hours and was then poured in saturated aqueous ammonium chloride solution (30 ml.). The mixture was extracted three times with diethyl ether (25 ml. each time) and the combined extracts were washed with saturated aqueous sodium chloride solution (25 ml.), dried over magnesium sulphate and evaporated to dryness. The mixture was purified by flash chromatography on a silica gel (Merck 9385) column using a 40:1 v/v mixture of methylene chloride and ethyl acetate as eluent. There was thus obtained, as an oil, 4-(4-cyano-3-trifluoromethylphenyl)-1-(3-hydroxy-3-p-methoxyphenylpropyl)thio-2-trifluoromethylbut-trans-3-en-2-ol.

The process described above was repeated using the appropriate isothiouronium bromide (or chloride, indicated by an asterisk* in the table) and the appropriate epoxide as starting materials, and there were thus obtained the compounds described in the following table:

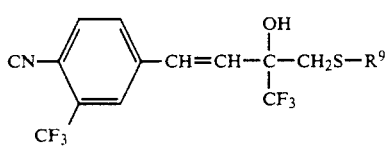

| R⁹ | m.p. (°C.) |
|---|---|
| (CH₂)₃OH | (oil) |
| (CH₂)₃COCH₃ | (oil)* |
| (CH₂)₃COC₆H₅ | 67-70 |
| (CH₂)₃CO-2-thienyl | (oil)* |
| CH₂-3-fluorophenyl | 85-86 |
| (CH₂)₃-4-methylthiophenyl | (oil)* |
| (CH₂)₃-4-methylsulphonylphenyl | (oil)* |
| (CH₂)₃-4-methoxyphenyl | (oil) |
| (CH₂)₄C₆H₅ | 66-69 |
| (CH₂)₂OC₆H₅ | 83-85 |
| (CH₂)₃OC₆H₅ | 63-65 |
| (CH₂)₃O-4-methylthiophenyl | (oil)* |
| (CH₂)₂CHOH-4-methylthiophenyl | (oil) |
| (CH₂)₂CHOH-4-methylsulphonylphenyl | (oil) |
| (CH₂)₃CHOHC₆H₅ | (oil) |
| CH₂CH=CHC₆H₅ (trans-) | 130-132 |

There was also obtained by a similar process 4-(3-chloro-4-cyanophenyl)-1-(4-methylsulphonylbenzyl)thio-2-trifluoromethylbut-trans-3-en-2-ol, using 4-methylsulphonylbenzylisothiouronium bromide as starting material.

The isothiouronium salts used as starting materials in Examples 2 and 3 were prepared by conventional means from thiourea and the appropriate alkyl halide or tosylate. Those which are novel and which were characterised by melting point are described in the following table:

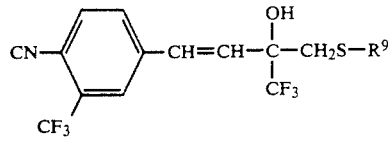

| R⁹ | X⊖ | m.p. (°C.) |
|---|---|---|
| (CH₂)₃C₆H₅ | Br | 118-119 |
| CH₂-3-methylsulphonylphenyl | Cl | 199-202 |
| CH₂-(2-methylthiazol-4-yl) | Cl | 168-170 |
| CH₂CH(OCH₃)CH₂OCH₃ | tosylate | 105-106 |
| (CH₂)₂O-4-methylsulphonylphenyl | Br | 165-167 |
| (CH₂)₃COCH₃ | Cl | 139-142 |
| (CH₂)₃CO-2-thienyl | Cl | 112-114 |
| (CH₂)₃-4-methylthiophenyl | Cl | 118-121 |
| (CH₂)₃-4-methylsulphonylphenyl | Cl | 161-166 |
| (CH₂)₃O-4-methylthiophenyl | Cl | 123-126 |
| (CH₂)₂CHOH-4-methylthiophenyl | Br | 188 |

EXAMPLE 4

A solution of potassium peroxymonosulphate (1.0 g.) in water (10 ml.) was added to a stirred solution of 4-(3,4-dichlorophenyl)-1-[(2-methylthioethyl)thio]-2-trifluoromethylbut-trans-3-en-2-ol (Example 1; 0.1 g.) in methanol (10 ml.) and the mixture was stirred at laboratory temperature for 16 hours, diluted with water (20 ml.) and extracted with ethyl acetate. The extract was washed with saturated aqueous sodium chloride solution, dried over magnesium sulphate and evaporated to dryness under reduced pressure, and the residue was purified by chromatography on a silica gel column using a 1:1 v/v mixture of petroleum ether (b.p. 60°-80°

C.) and ethyl acetate as eluent. There was thus obtained 4-(3,4-dichlorophenyl)-1-[(2-methylsulphonylethyl)sulphonyl]-2-trifluoromethylbut-trans-3-en-2-ol, m.p.187° C.

The process described above was repeated using the appropriate thio-compound described in Example 1 or 3 above as starting material, and there were thus obtained the compounds described in the following table:

$$R^4-\text{C}_6\text{H}_3(R^3)-CH=CH-\underset{\underset{CF_3}{|}}{\overset{\overset{OH}{|}}{C}}-CH_2SO_2-R^{10}$$

| $R^3$ | $R^4$ | $R^{10}$ | m.p. (°C.) |
|---|---|---|---|
| Cl | Cl | $(CH_2)_2OCH_3$ | (oil) |
| Cl | Cl | $(CH_2)_3OCH_3$ | (oil) |
| $CF_3$ | CN | $(CH_2)_3OCH_3$ | (oil) |
| Cl | Cl | $(CH_2)_3SO_2CH_3$ | 130 |
| Cl | CN | $(CH_2)_3SO_2CH_3$ | 90 (d) |
| $CF_3$ | CN | $(CH_2)_3SO_2CH_3$ | 140 |
| Cl | Cl | $CH_2C_6H_5$ | (oil) |
| Cl | Cl | $(CH_2)_2$-4-fluorophenyl | (oil) |
| $CF_3$ | CN | $(CH_2)_2$-4-methyl-sulphonylphenyl | (oil) |
| $CF_3$ | CN | $(CH_2)_2SO_2C_6H_5$ | 155-165 |
| $CF_3$ | CN | $(CH_2)_2SO_2$-3-methyl-sulphonylphenyl | 72-74 |

EXAMPLE 5 n-Butyl-lithium (1.2 ml. of a 1.6 molar solution in hexane) was added dropwise to a stirred solution of (2-methoxyethoxy)methoxymethyl-tri-n-butylstannane (0.734 g., prepared by a similar process Chemical Society, 1978, 100, 1483) in tetrahydrofuran (100 ml.) which was maintained at −78° C. under an atmosphere of argon. The mixture was stirred at −78° C. for 15 minutes, a solution of 1-(3,4-dichlorophenyl)-4,4,4-trifluorobut-1-ene-3-one (0.44 g.) in tetrahydrofuran (10 ml) was added dropwise and the mixture was stirred for 2 hours at −78° C. Water (1 ml) was added, the mixture was allowed to warm up to laboratory temperature and diethy ether (20 ml) was added. The mixture was washed with saturated aqueous sodium chloride solution, dried over magnesium sulfate and evaporated to dryness. The residue was purified by flash chromatography on a silica gel (Merck 9385) column using a 1:1 v/v mixture of ethyl acetate and petroleum ether (b.p. 60°-80° C.) as eluent. There was thus obtained as an oil 1-(3,4-dichlorophenyl)-4-(2-methoxyethoxy)- methoxy-3-trifluoromethylbut-trans-1-en-3-ol.

What we claim is:

1. A compound of the formula

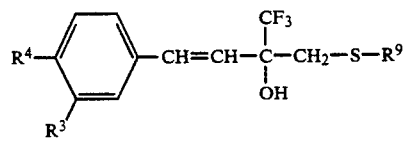

wherein $R^3$ and $R^4$, which may be the same or different, each is an electron withdrawing substituent selected from halogeno, nitro, cyano and trifluoromethyl, or each is hydrogen, provided that at least one of $R^3$ and $R^4$ is an electron withdrawing substituent; and wherein $R^9$ is alkyl of up to 6 carbon atoms which contains a substituent selected from ureido and carbamoyl, alkylcarbamoyl and alkanoylamino each of up to 6 carbon atoms, and dialkylcarbamoyl of up to 12 carbon atoms.

2. A compound as claimed in claim 1 wherein one or both of $R^3$ and $R^4$, which may be the same or different, are fluoro, chloro cyano, trifluoromethyl or nitro, the other of $R^3$ and $R^4$ being hydrogen; and wherein $R^9$ is straight-chain alkyl of up to 4 carbon atoms which bears one substituent selected from carbamoyl, acetamido, ureido and dimethylcarbamoyl.

3. A compound as claimed in claim 1 wherein both of $R^3$ and $R^4$ is chloro, $R^3$ is chloro and $R^4$ is cyano, or $R^3$ is trifluoromethyl and $R^4$ is cyano or fluoro.

4. The compound 1-(2-carbamoylethylthio)- or 1-(2-N,N-dimethylcarbamoylethylthio)-4-(4-cyano-3-trifluoromethylphenyl)-2-trifluoromethylbut-trans-3-en-2-ol.

5. The compound 1-(2-carbamoylethylthio)-4-(3-chloro-4-cyano-phenyl)-2-trifluoromethylbut-trans-3-en-2-ol.

6. A pharmaceutical or veterinary composition having antiandrogenic properties which comprises an amount of a compound claimed in any of claims 1 to 5 sufficient to exert an antiandrogenic effect in association with a pharmaceutically-acceptable diluent or carrier.

7. A method for producing an antiandrogenic effect in a warm-blooded animal which comprises administering to said animal an amount of a compound claimed in claim 1 sufficient to exert said antiandrogenic effect.

* * * * *